United States Patent
Clerc et al.

(10) Patent No.: US 10,398,540 B2
(45) Date of Patent: Sep. 3, 2019

(54) STENT FOR REPAIR OF ANASTOMASIS SURGERY LEAKS

(75) Inventors: Claude Clerc, Marlborough, MA (US);
Chris Thompson, Needham, MA (US);
Christopher Dubois, Lincoln, RI (US);
Barry Weitzner, Acton, MA (US);
Gary Jordan, Litchfield, NH (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 774 days.

(21) Appl. No.: 13/097,520

(22) Filed: Apr. 29, 2011

(65) Prior Publication Data

US 2011/0307070 A1  Dec. 15, 2011

Related U.S. Application Data

(60) Provisional application No. 61/329,893, filed on Apr. 30, 2010.

(51) Int. Cl.
*A61F 2/04* (2013.01)
*A61B 17/11* (2006.01)
(Continued)

(52) U.S. Cl.
CPC .......... *A61F 2/04* (2013.01); *A61B 17/1114* (2013.01); *A61F 2/90* (2013.01); *A61F 5/0076* (2013.01); *A61L 31/10* (2013.01); *B29C 41/06* (2013.01); *B29C 41/20* (2013.01); *A61B 2017/00526* (2013.01); *A61B 2017/00884* (2013.01); *A61B 2017/00893* (2013.01); *A61F 2/07* (2013.01); *A61F 2/2418* (2013.01); *A61F 2/91* (2013.01); *A61F 2002/045* (2013.01); *A61F 2002/821* (2013.01); *A61F 2002/823* (2013.01); *A61F 2210/0004* (2013.01); *A61F 2210/0014* (2013.01); *A61F 2210/0076* (2013.01); *A61F 2230/0067* (2013.01); *A61F 2230/0071* (2013.01); *A61F 2230/0078* (2013.01);
(Continued)

(58) Field of Classification Search
CPC ...... A61F 2/04; A61F 2/042; A61F 2002/041; A61F 2002/043; A61F 2002/044; A61F 2002/045; A61F 2002/046; A61F 2002/047; A61F 2002/048; A61B 17/11; A61B 17/1114; A61B 2017/111; A61B 2017/1132; A61B 2017/1135; A61B 2017/1139
USPC ............... 604/8–9; 623/1.15–1.16, 1.3–1.31, 623/23.64–23.7, 2.17–2.19, 2.38–2.41, 623/8–9; 1/8–9; 606/213–221
See application file for complete search history.

(56) References Cited

U.S. PATENT DOCUMENTS 6,110,198 A * 8/2000 Fogarty ..................... A61F 2/07
128/898
6,156,064 A * 12/2000 Chouinard ................ A61F 2/07
623/1.44
(Continued)

FOREIGN PATENT DOCUMENTS

WO   WO 2007062661 A2 *  6/2007   ............... A61F 2/88

*Primary Examiner* — Andrew M Iwamaye
(74) *Attorney, Agent, or Firm* — Seager, Tufte & Wickhem, LLP

(57) ABSTRACT

A stent for repairing post-anastomasis (e.g., bariatric) surgery leaks is formed by an elongated tube having a proximal flare-shaped flange, an enlarged middle section, and a distal flare-shaped flange, where an exterior surface of the elongated tube is substantially covered with a polymer.

20 Claims, 10 Drawing Sheets

(51) Int. Cl.
    *A61F 2/90*         (2013.01)
    *A61F 5/00*         (2006.01)
    *A61L 31/10*       (2006.01)
    *B29C 41/06*      (2006.01)
    *B29C 41/20*      (2006.01)
    *A61F 2/82*         (2013.01)
    *A61F 2/07*         (2013.01)
    *A61B 17/00*      (2006.01)
    *A61F 2/24*         (2006.01)
    *A61F 2/91*         (2013.01)

(52) U.S. Cl.
    CPC ... *A61F 2240/001* (2013.01); *A61F 2250/001* (2013.01); *A61F 2250/0032* (2013.01); *A61F 2250/0037* (2013.01); *A61F 2250/0039* (2013.01); *A61F 2250/0098* (2013.01)

(56) References Cited

U.S. PATENT DOCUMENTS

| | | | |
|---|---|---|---|
| 6,299,637 B1* | 10/2001 | Shaolian | A61F 2/2418 623/1.24 |
| 6,340,368 B1* | 1/2002 | Verbeck | 623/1.34 |
| 6,562,066 B1* | 5/2003 | Martin | 623/1.15 |
| 8,317,856 B2* | 11/2012 | Shalev | A61F 2/07 623/1.13 |
| 2002/0143385 A1* | 10/2002 | Yang | A61F 2/07 623/1.13 |
| 2003/0040804 A1 | 2/2003 | Stack et al. | |
| 2003/0130719 A1* | 7/2003 | Martin | 623/1.13 |
| 2003/0199991 A1* | 10/2003 | Stack et al. | 623/23.65 |
| 2005/0143805 A1* | 6/2005 | Hierlemann | A61F 2/04 623/1.15 |
| 2006/0155364 A1* | 7/2006 | Holloway et al. | 623/1.16 |
| 2006/0190075 A1* | 8/2006 | Jordan | A61F 2/90 623/1.23 |
| 2006/0271161 A1* | 11/2006 | Meyer | A61F 2/856 623/1.15 |
| 2007/0100435 A1* | 5/2007 | Case et al. | 623/1.24 |
| 2007/0162103 A1* | 7/2007 | Case et al. | 623/1.13 |
| 2009/0182404 A1* | 7/2009 | Shokoohi | 623/1.11 |
| 2009/0192588 A1 | 7/2009 | Shin et al. | |
| 2009/0210048 A1* | 8/2009 | Amplatz | A61F 2/07 623/1.13 |
| 2009/0248132 A1* | 10/2009 | Bloom et al. | 623/1.15 |
| 2010/0094409 A1* | 4/2010 | Barker | A61F 2/07 623/1.46 |
| 2010/0100105 A1 | 4/2010 | Bates et al. | |
| 2010/0121461 A1* | 5/2010 | Sobrino-Serrano | A61F 2/04 623/23.68 |

* cited by examiner

US 10,398,540 B2

STENT FOR REPAIR OF ANASTOMASIS SURGERY LEAKS

CROSS-REFERENCE TO RELATED APPLICATIONS

This application claims the benefit of U.S. Provisional Patent Application No. 61/329,893, entitled "STENT FOR REPAIR OF ANASTOMOSIS SURGERY LEAKS, AND METHODS OF MANUFACTURING AND USING THE SAME," and filed Apr. 30, 2010, the entire disclosure of which is incorporated herein by reference.

FIELD OF THE INVENTION

The disclosed inventions pertain to stents configured for repairing post-anastomasis (e.g., bariatric) surgery leaks, and to methods for their manufacture and use.

BACKGROUND OF THE INVENTION

Obesity is a medical condition in which excess body fat has accumulated to the extent that it may have an adverse effect on health, leading to reduced life expectancy and/or increased health problems. Body mass index (BMI), a measurement which compares weight and height, defines people as overweight (pre-obese) when their BMI is between 25 kg/m$^2$ and 30 kg/m$^2$, and obese when it is greater than 30 kg/m$^2$. Obesity is most commonly caused by a combination of excessive dietary calories, lack of physical activity, and genetic susceptibility. On average, obesity reduces life expectancy by six to seven years. Obesity increases the likelihood of various diseases, particularly heart disease, type 2 diabetes, breathing difficulties during sleep, certain types of cancer, and osteoarthritis. Obesity is a leading preventable cause of death worldwide, with increasing prevalence in adults and children, and authorities view it as one of the most serious public health problems of the 21st century. The WHO estimated in 2005 that at least 400 million adults (9.8%) worldwide were obese. According to a CDC report, 34% of adults and 17% of children in the United States were obese in 2007-2008. Obesity has been estimated to cause up to 365,000 deaths per year in the United States.

Bariatric (or weight loss) surgeries are surgical treatments for treating severe obesity (BMI greater than 40 kg/m$^2$). The most common bariatric surgery is Roux-en-Y (FIG. 1), in which a small gastric pouch and an alimentary limb (Roux limb) are created and anastomosed to one another and to the patient's jejunum, bypassing part of the small intestine. Other bariatric surgeries, as shown in FIG. 2, may involve removal of a portion of the stomach (sleeve gastrectomy or biliopancreatic diversion with duodenal switch). In biliopancreatic diversion with duodenal switch, about 80 percent of the stomach is removed, forming a thin sleeve-like stomach. The valve that releases food to the small intestine remains (pylorus) along with a limited portion of the small intestine that normally connects to the stomach (duodenum). The surgery bypasses the majority of the intestine by connecting the end portion of the intestine to the duodenum near the stomach (biliopancreatic diversion). This weight-loss surgery is effective but has more risks, such as malnutrition and vitamin deficiencies, and requires close monitoring. It is generally used for people who have a body mass index greater than 50 kg/m$^2$. About 150,000 patients undergo bariatric surgery each year. Long-term studies show the procedures cause significant long-term loss of weight, recovery from diabetes, improvement in cardiovascular risk factors, and a reduction in mortality of 23% to 40%.

It is reported that post operative leaks occur in about 2% to 3% of bariatric surgery cases, but the real number may be higher due to underreporting. Leaks mostly occur along the stapling line of the gastric pouch and at the gastrojejunal anastomosis. However, leaks can also occur along the Z line between the esophagus and the stomach. Leaks are one of the most dreaded complications after bariatric surgery and are associated with increased morbidity and mortality. Leaks can be treated with several modalities, including site drainage with parenteral nutrition and bowel rest, various endoscopic methods (esophageal stents, clips, glue, sutures), and a second bariatric surgery. These treatment modalities all have drawbacks.

SUMMARY OF THE INVENTION

In one embodiment of the disclosed inventions, a stent for repairing post-anastomasis (e.g., bariatric) surgery leaks comprises an elongated tube having a proximal flare-shaped flange, an enlarged middle section, and a distal flare-shaped flange, wherein an exterior surface of the elongated tube is substantially covered with a polymer, such as an elastomeric polymer. The elongated tube may be self expanding, and may be formed from an alloy or from a polymer. The stent may be of a woven type, and may further comprise a removal loop. Optionally, the exterior surface of the elongated tube is coated with a drug. Optionally, some or all of the stent and/or covering may be biodegradable. The polymer covering may swell in situ to aid in leakage prevention.

In another embodiment of the disclosed inventions, a method of manufacturing a stent configured for repairing post-anastomasis (e.g., bariatric) surgery leaks comprises forming a stent having a middle bulge around a mandrel, and removing the mandrel from an interior of the stent.

In some embodiments, the mandrel comprises an expandable component (e.g., a balloon or a basket) configured to form the middle bulge, wherein removal of the mandrel comprises reducing the expandable component in order to remove it from the stent interior. In one embodiment, the mandrel comprises a plurality of elements that may be disassembled and removed from the stent interior.

In another embodiment, the mandrel comprises a first coaxial section slidably disposed inside of a second coaxial section, wherein forming a stent having a middle bulge includes sliding the first and second coaxial sections away from each other to extend the mandrel, forming a stent around the extended mandrel, securing a first part of the stent to the first coaxial section, securing a second part of the stent to the second coaxial section, and sliding the first and second coaxial sections toward each other to create a middle bulge between the first and second parts of the stent.

In yet another embodiment, the step of removing the mandrel comprises destroying the mandrel.

The formed stent may be covered by inserting the formed stent into an interior of a mold configured to mimic its exterior shape, adding covering solution to the interior of the mold, rotating and tilting the mold about a center axis to cover the formed stent with the covering solution, and removing the covered stent from the mold. Such processes for coating or covering the stent are referred to as sandwiching and electro-spinning.

In still another embodiment of the disclosed inventions, a method of repairing post-anastomasis (e.g., bariatric) surgery leaks in a patient includes mounting a shape memory polymer stent on an expandable device, such as an inflatable balloon or a mechanically expandable basket, inserting the expandable device having the stent mounted thereon into a body lumen of the patient proximate a site of a post-anastomasis surgery leak to be repaired, expanding the expandable device to thereby expand the stent against the leak, reducing the size of the expandable device while maintaining the expanded size of the stent, and removing the expandable device from the stent through the body lumen. Such surgical method may further include applying heat to soften and remove stent after the leaks have been allowed to heal.

Other and further aspects and features of embodiments of the disclosed inventions will become apparent from the ensuing detailed description in view of the accompanying figures.

BRIEF DESCRIPTION OF THE DRAWINGS

Referring now to the drawings, in which like reference numbers represent corresponding parts throughout:

In FIGS. 9a and 9b, the mandrel is fully extended. In FIG. 9c, the mandrel is shortened.

DETAILED DESCRIPTION OF THE ILLUSTRATED EMBODIMENTS

The following Detailed Description of the Illustrated Embodiments, and of alternate embodiments not shown, is provided for purposes of explaining the inventive concepts disclosed herein, and not for purposes of limitation of the appended claims. In particular, while the Detailed Description of the Illustrated Embodiments is directed to the repair of post-bariatric surgery leaks, in a broader aspect, the disclosed inventions are not limited to devices and methods of their manufacture and use for treatment of bariatric leaks, but are also applicable to the treatment of leaks resulting from any anastomosis surgery, i.e., between body lumens and/or between body lumens and organs, and in particular between body lumens and/or organs in the GI system. Embodiments of the disclosed inventions may also be useful for treatment following full thickness resection procedures and/or urology procedures such as a radical prostatectomy.

Figure 3:
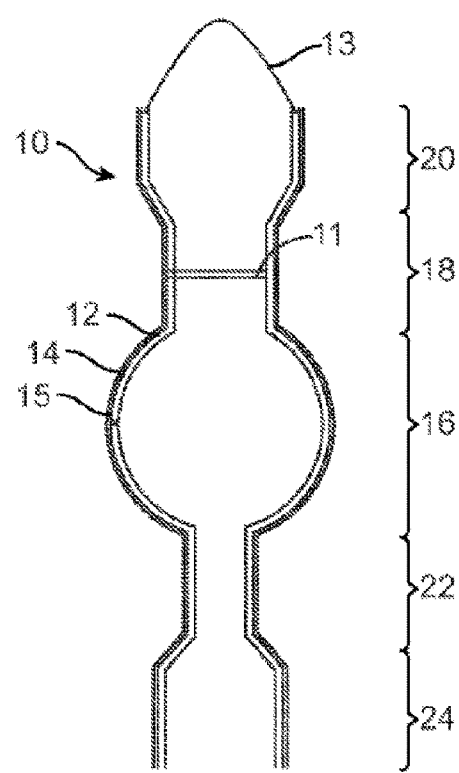
FIG. 3 is a longitudinal cross-section view of a stent constructed according to one embodiment of the disclosed inventions.

FIG. 3 illustrates a single stent 10 configured to temporarily seal leaks after a Roux-en-Y bariatric surgery and to be removed after the leaks have healed. The stent 10 is designed to seal the locations where leaks are most likely to occur. The stent 10 is formed of a single elongated tubular member 12 that is substantially covered with a polymer 14 to seal leaks and to prevent tissue in-growth, which would complicate removal after the leaks have healed. The tubular member 12 is shaped to prevent distal or proximal migration. The tubular member 12 has an enlarged middle segment 16 configured to sit in the gastric pouch and prevent distal or proximal migration. The middle segment 16 also prevents stagnation of food or liquid in the stomach by filling the gastric pouch. In one embodiment, the middle segment 16 is an approximate sphere with a diameter of about 39 mm configured to fill a 30 ml gastric pouch. Proximal of the middle segment 16 is a proximal cylindrical segment 18 configured to extend from the distal esophagus into the proximal stomach, bridging the Z line. In one embodiment, the proximal cylindrical segment 18 is about 20 mm in length and about 20 mm in cross-sectional diameter.

Proximal of the proximal cylindrical segment 18 is a proximal flare-shaped flange 20 configured to expand along the wall of the distal esophagus to prevent any food or liquid from passing between the stent and the enteral wall. In one embodiment, the proximal flange 20 is about 20 mm in length and about 30 mm in cross-sectional diameter at its widest point. Distal of the middle segment 16 is a distal cylindrical segment 22 configured to extend from the distal stomach into the jejunum, bridging the gastro jejunal anastomosis and the Roux limb. In one embodiment, the distal cylindrical segment 22 is about 20 to 70 mm in length and about 12 mm in cross-sectional diameter. Distal of the distal cylindrical segment 22 is a distal flare-shaped flange 24 configured to expand along the wall of the jejunum to prevent any food or liquid from passing between the stent and the enteral wall. In one embodiment, the distal flange 24 is about 20 mm in length and about 22 mm in cross-sectional diameter at its widest point.

The tubular member 12 can be formed from alloys such as Elgiloy® and Nitinol® or polymers such as polyethylene terephthalate (PET), like a Polyflex® stent, and may also be made of a radiopaque material. In some embodiments, the tubular member 12 is made of a biodegradable polymer and substantially covered with a biodegradable polymer 14, and is also radiopaque. The tubular member 12 can have a woven structure (i.e., constructed from one or more filaments). In one embodiment, the tubular member 12 is braided with one filament. In other embodiments, the tubular member 12 is braided with several filaments, as is found, for example, in the WallFlex®, WALLSTENT® and Polyflex® stents made and distributed by Boston Scientific. In still another embodiment, the tubular member 12 is knitted, such as the Ultraflex™ stents made by Boston Scientific. In yet another embodiment, the tubular member 12 is of a knotted type, such the Precision Colonic™ stents made by Boston Scientific. In still another embodiment, the tubular member 12 is laser cut, such as the EPIC™ stents made by Boston Scientific. Alternatively, the tubular member 12 can be a combination of any of the above-mentioned stent types. In some embodiments, the stent 10 is self-expanding due to the combination of materials from which the stent 10 is made and the techniques used to make the stent. Fibers used to make the tubular member 12 may be cored fibers, e.g., having a Nitinol™ outer shell and a platinum core. Reference is made to the stents disclosed in U.S. Pat. No. 7,101,392 (Heath), and U.S. Pat. No. 6,527,802 (Mayer), the contents of which are fully incorporated herein by reference.

The exterior surface of the tubular member 12 may be substantially covered with a polymer 14, which may be resistant to degradation. In various embodiments, the polymer can be silicone, styrene isoprene butadiene (SIBS), expanded polytetrafluoroethylene (ePTFE or expanded Teflon®), or polyurethane. Substantially covering the tubular member 12 with polymer 14 improves the stents 10 ability to occlude leaks. In this regard, the polymer 14 may be made of a material that swells and/or coated with an agent that swells in situ. The polymer 14 also reduces tissue in-growth, which facilitates removal after the leaks have healed, e.g., between 2 to 8 weeks after implantation.

In some embodiments, the stent 10 comprises a valve 11 to prevent reflux. The valve 11 is located in the proximal cylindrical segment 18 or distal cylindrical segment 22 and is configured to allow flow in the distal direction and prevent flow in the proximal direction. In other embodiments, the stent 10 comprises a removal loop 13 to facilitate removing the stent 10 by pulling proximally. In still other embodiments, the stent 10 is coated with a drug configured to improve healing or, more generally, a therapeutic agent. In yet other embodiments, the stent 10 includes radiopaque markers 15 for fluoroscopic positioning.

Figure 4:
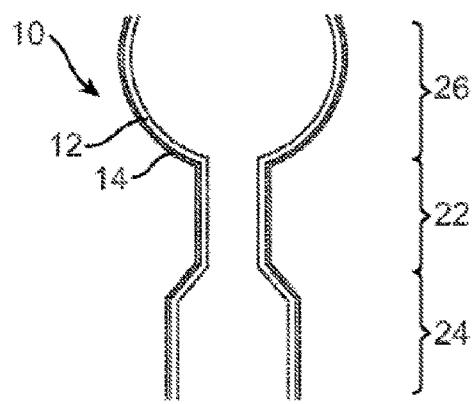
FIG. 4 is a longitudinal cross-section view of a stent constructed according to another embodiment of the disclosed inventions.

The stent 10 in FIG. 4 is configured to temporarily seal leaks at the gastro jejunal anastomosis after a Roux-en-Y bariatric surgery and to be removed after the leaks have healed. The distal cylindrical segment 22 and the distal flair-shaped flange 24 are identical to the corresponding parts in the stent 10 in FIG. 3. Proximal of the distal cylindrical segment 22 is a gastric flange 26, configured to sit in the distal gastric pouch and prevent any food or liquid from passing between the stent and the enteral wall. The gastric flange 26 also cooperates with the distal flange 24 to prevent distal or proximal migration of the stent 10. In one embodiment, the gastric flange 26 is a bowl with a length of about 20-30 mm and a diameter of about 40 mm at its widest point. This stent 10 is similar to distal half of the stent 10 in FIG. 3. In alternative embodiments, the flange 26 may take any open shape, such as, e.g., a bowl, a truncated cone, a saucer, etc.

Figure 1:
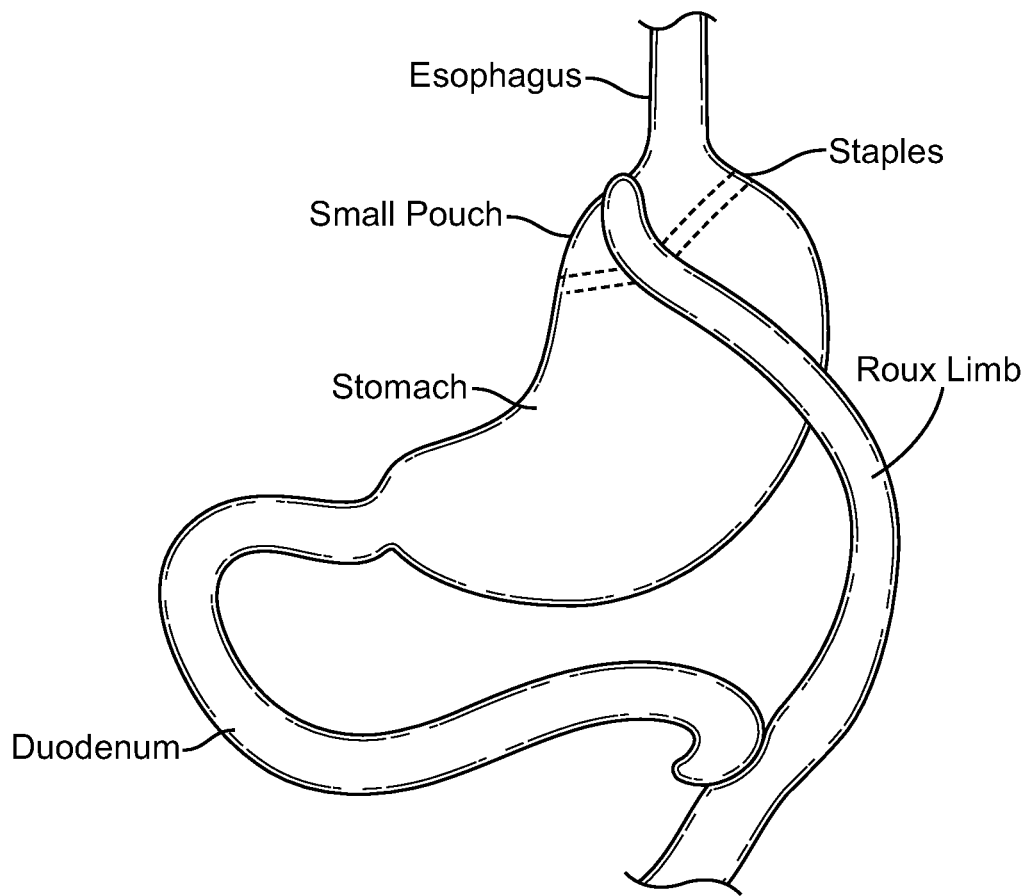
FIG. 1 is a schematic view of portions of an alimentary canal after a Roux-en-Y procedure.
Figure 2:
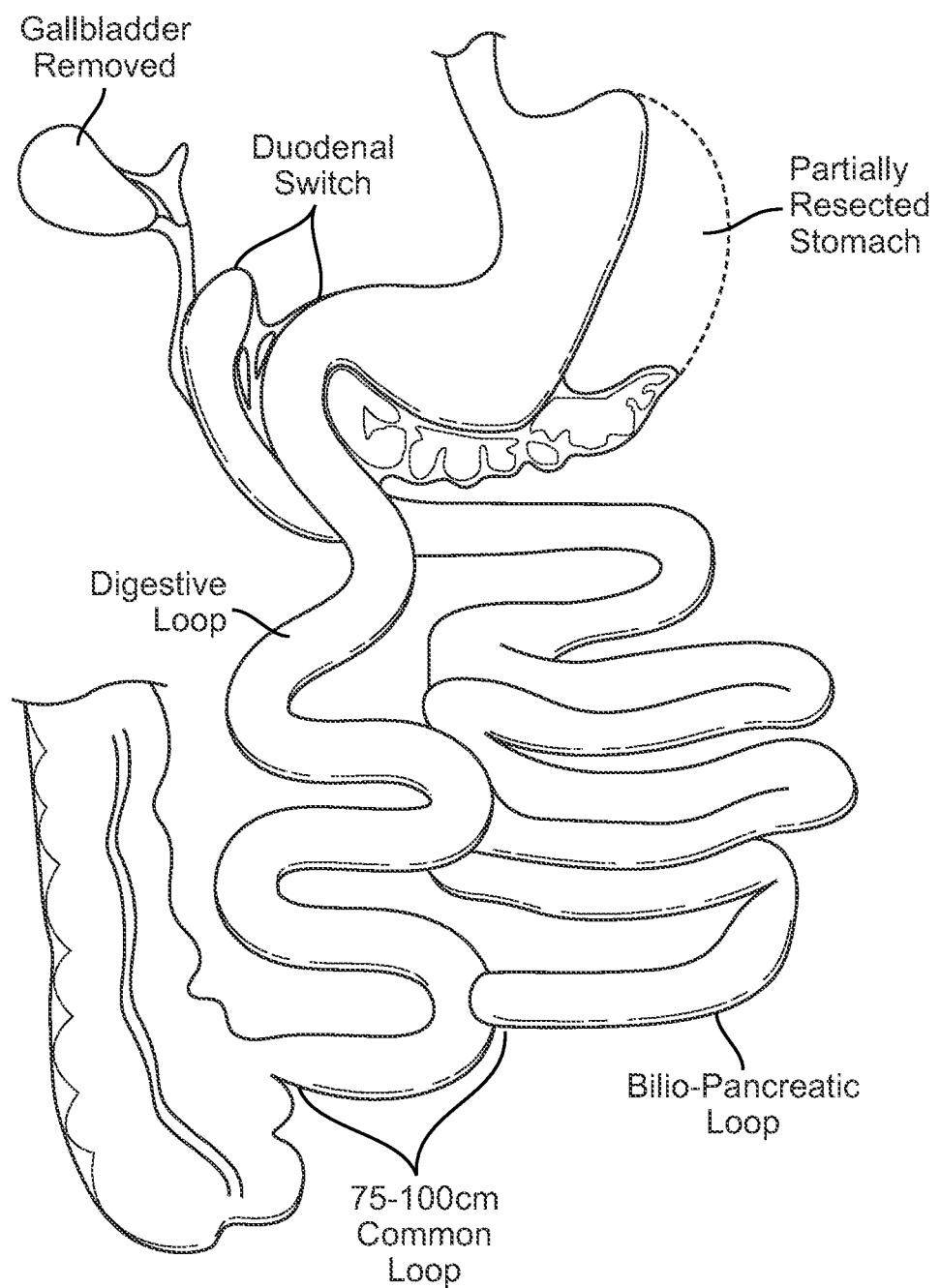
FIG. 2 is a schematic view of portions of an alimentary canal after a biliopancreatic diversion with duodenal switch procedure.
Figure 5:
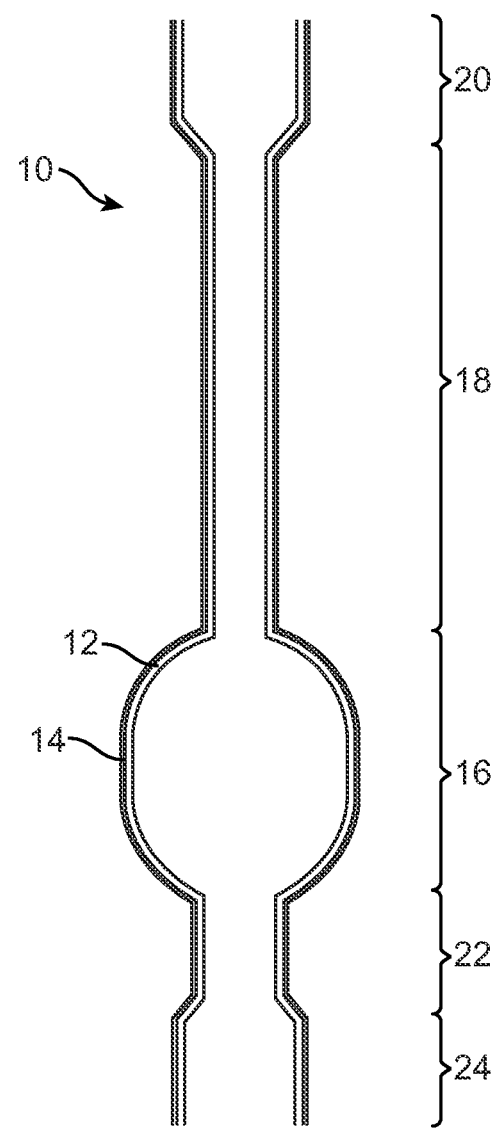
FIG. 5 is a longitudinal cross-section view of a stent constructed according to yet another embodiment of the disclosed inventions.

The stent 10 in FIG. 5 is configured to temporarily seal leaks after a sleeve gastrectomy or a biliopancreatic diversion with duodenal switch, and to be removed after the leaks have healed. After these procedures, the stomach pouch is long and thin, as shown in FIG. 2. Accordingly, stents 10 used for sealing leaks after these procedures have a longer segment in the stomach. Such stents 10 are designed to seal the locations where leaks are most likely to occur after these procedures (i.e., Z line, stomach staple line, duodeno-jejunal anastomosis). The stent 10 may comprise an elongated tubular member 12 that is substantially covered with a polymer 14 as described above. The tubular member 12 is shaped to prevent distal or proximal migration.

The tubular member 12 has an enlarged middle segment 16 configured to sit in the stomach antrum and prevent distal or proximal migration. In one embodiment, the middle segment 16 has an ovoid shape with a length of about 60 mm and a cross-sectional diameter of about 50 mm at its widest point. The middle segment 16 is configured to sit in the antrum of the stomach and cooperates with the proximal and distal flanges 20, 24 to prevent distal or proximal migration of the stent 10.

Proximal of the middle segment 16 is a proximal cylindrical segment 18 configured to extend from the distal esophagus into the proximal stomach, bridging the Z line. In one embodiment, the proximal cylindrical segment 18 is about 260 mm in length and about 15 mm in cross-sectional diameter. Proximal of the proximal cylindrical segment 18 is a proximal flare-shaped flange 20 configured to expand along the wall of the distal esophagus to prevent any food or liquid from passing between the stent and the enteral wall. In one embodiment, the proximal flange 20 is about 20 mm in length and about 30 mm in cross-sectional diameter at its widest point. Distal of the middle segment 16 is a distal cylindrical segment 22 configured to extend from the distal stomach, through the duodenum and into the jejunum, bridging the duodeno-jejunal anastomosis. In one embodiment, the distal cylindrical segment 22 is about 50 mm in length and about 20 mm in cross-sectional diameter. Distal of the distal cylindrical segment 22 is a distal flare-shaped flange 24 configured to expand along the wall of the jejunum to prevent any food or liquid from passing between the stent and the enteral wall. In one embodiment, the distal flange 24 is about 20 mm in length and about 30 mm in cross-sectional diameter at its widest point. The same stent shape can also be used to treat leaks after sleeve gastrectomy.

Figure 6A:
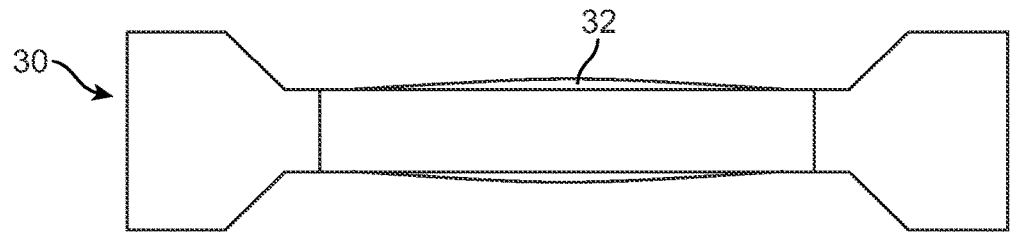
FIGS. 6a and 6b are respective deflated and inflated longitudinal cross-section views of a mandrel according to one embodiment of the disclosed inventions.
Figure 6B:
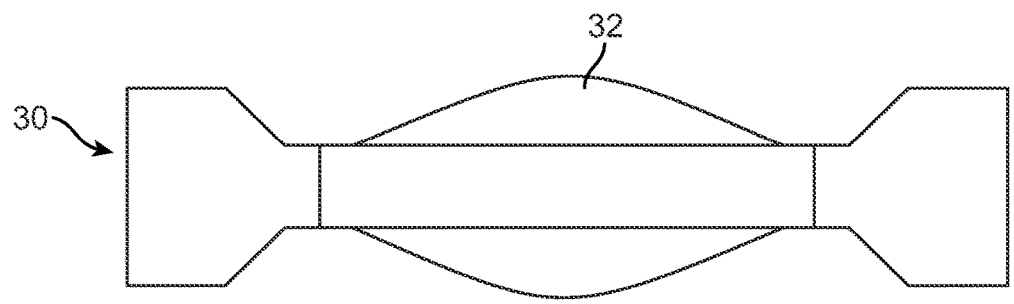

The dimensions of the above-described embodiments are provided for illustration and not limitation. One of skill in the art will recognize that the dimensions of the stent 10 can be modified to fit various anatomies. Because some embodiments of the stent 10 include an enlarged middle segment 16, various mandrels 30 have been designed to facilitate removal of the mandrel 30 after forming the stent 10 around the mandrel 30. The mandrel 30 in FIGS. 6a and 6b has an inflatable component 32 in the middle of the mandrel 30. Either during or after forming the stent 10 around the mandrel 30, the inflatable component 32 is inflated to form the enlarged middle segment 16 of the stent 10. After the stent 10 is formed, e.g., braided and heat-treated, the inflatable component 32 is deflated and the mandrel 30 is removed from the stent 10 by disconnecting one of the enlarged flange forming end pieces from the mandrel 30.

Figure 7:
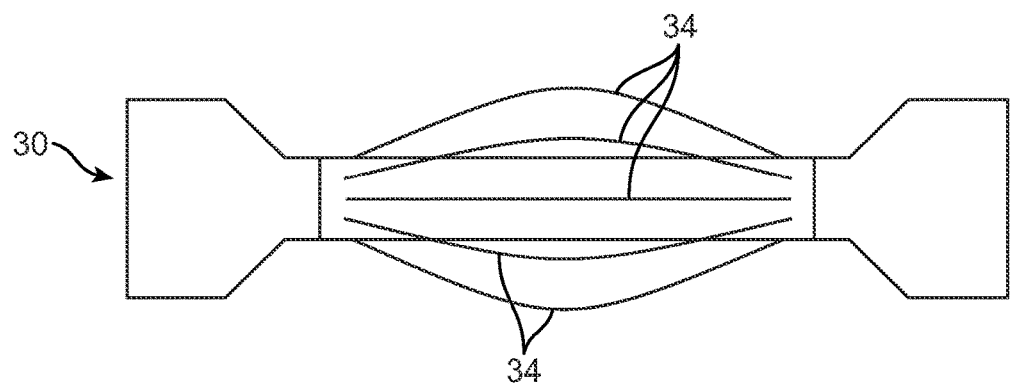
FIG. 7 is a perspective view of a mandrel according to yet another embodiment of the disclosed inventions.
Figure 8A:
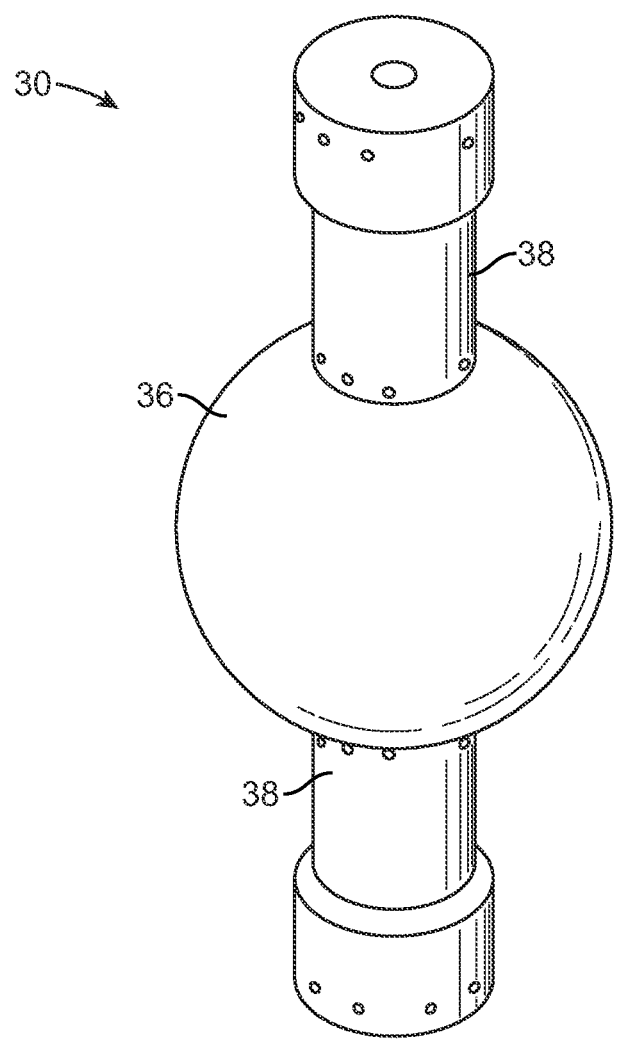
FIGS. 8a and 8b are respective assembled and disassembled perspective views of a mandrel according to yet another embodiment.

The mandrel 30 in FIG. 7 has wire elements 34 releasably attached to the middle of the mandrel 30 and configured to form the enlarged middle segment 16 of the stent 10. After the stent 10 is formed around the mandrel 30, the wire elements 34 are released from the mandrel 30 and removed from the stent 10 along with the rest of the mandrel 30. The mandrel 30 in FIGS. 8a and 8b has a core 36 and two end pieces 38. In some embodiments, the elements 34 are flat strips. When the mandrel 30 is assembled (FIG. 8a), the core 36 is configured to form the enlarged middle segment 16 of the stent 10. For example, the elements may be configured to bow outwardly by axial movement of the mandrel towards the other end.

Figure 8B:
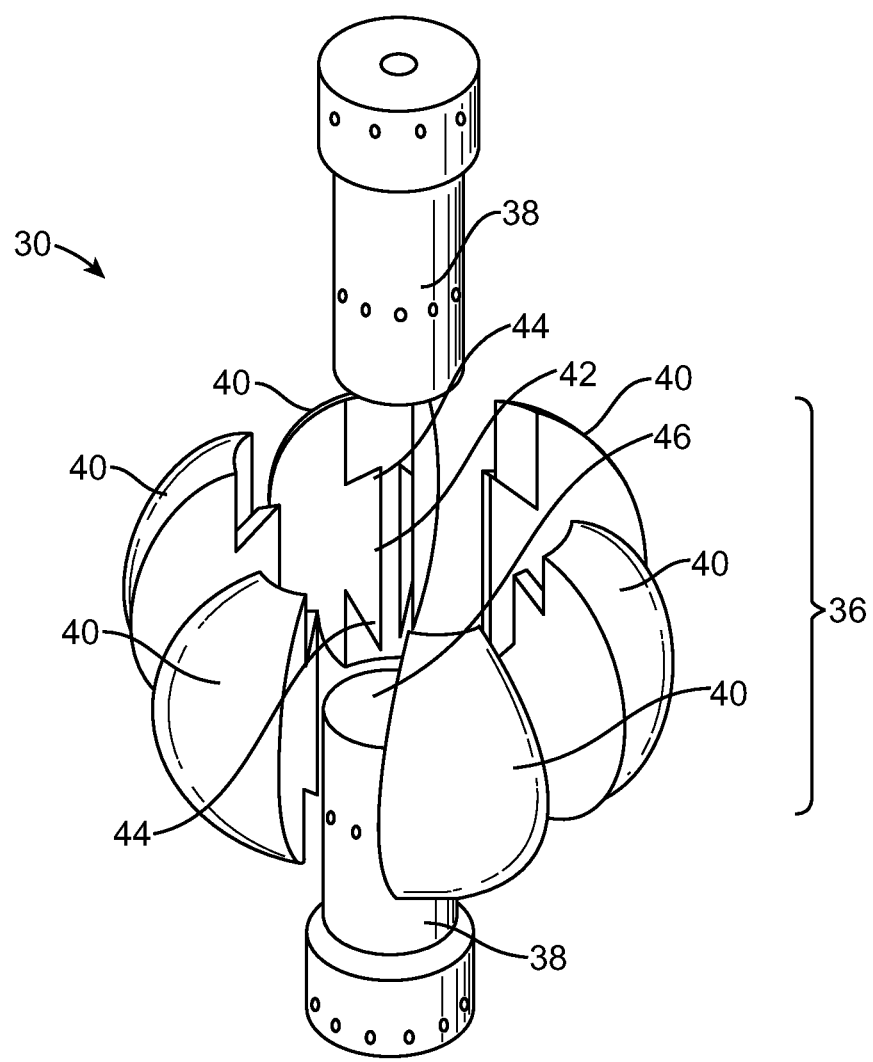

After the stent 10 is formed around the mandrel 30, the core 36 is disassembled as in FIG. 8b and removed from the stent 10 along with the end pieces 38. As shown in FIG. 8b, the core 36 may include six slices 40 that each has a projection 42 with two polar notches 44. Each of the end pieces 38 has a recess 46 into which one polar notch 44 from each slice 40 sits when the mandrel 30 is assembled to hold the core 36 together. Accordingly, the core 36 can be dissembled by pulling the end pieces 38 apart from each other. In some embodiments, the slices 40 are cored out or hollowed to facilitate their removal from the stent 10. It will be appreciated that fewer or more end pieces 38 and/or slices 40 may be employed in alternate embodiments.

Figure 9A:
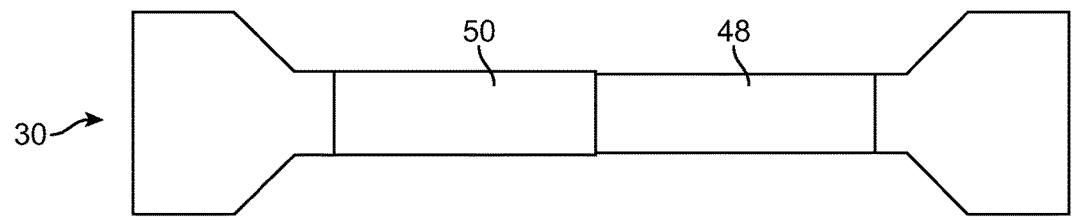
FIGS. 9a, 9b and 9c are respective perspective views of a mandrel according to still another embodiment of the disclosed inventions.
Figure 9B:
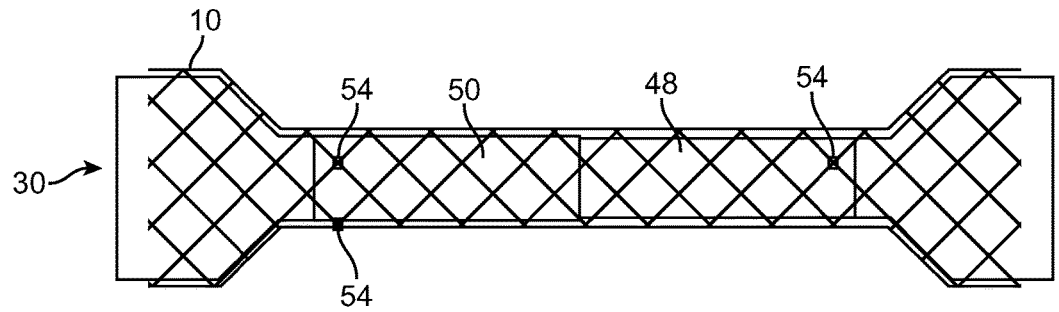
Figure 9C:
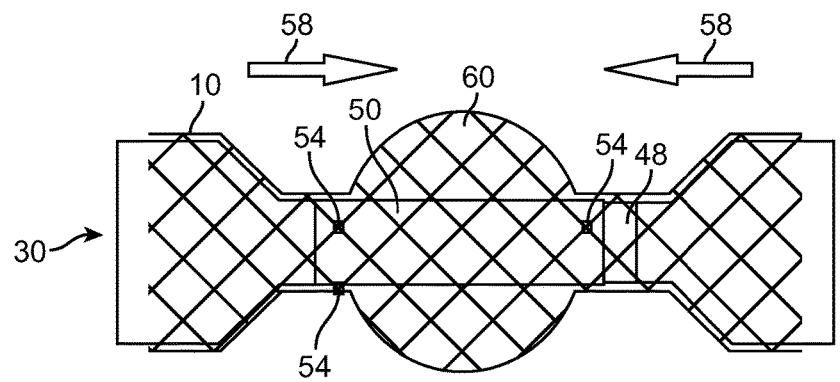

The mandrel 30 in FIGS. 9a, 9b, and 9c is made of a first coaxial section 48 that is slidably disposed in a second coaxial section 50. First the coaxial sections 48, 50 are pulled apart from each other, as shown in FIG. 9a, such that the mandrel 30 is at its maximum length. Then the stent 10 is formed (but not set) around the elongated mandrel 30 and attached to the mandrel 30 at bonding points 54, as shown in FIG. 9b. Next the coaxial section 48, 50 are pushed toward 58 each other, as shown in FIG. 9c. This motion 58 along with the attachment of the stent 10 to the mandrel 30 causes the middle of the mandrel 30 to displace radially and form the enlarged middle segment 16 of the stent 10. Then the stent 10 is set and the mandrel 30 is removed from the stent 10. In other embodiments, the mandrel 30 is removed from the stent 10 by destroying the mandrel 30.

Figure 10:
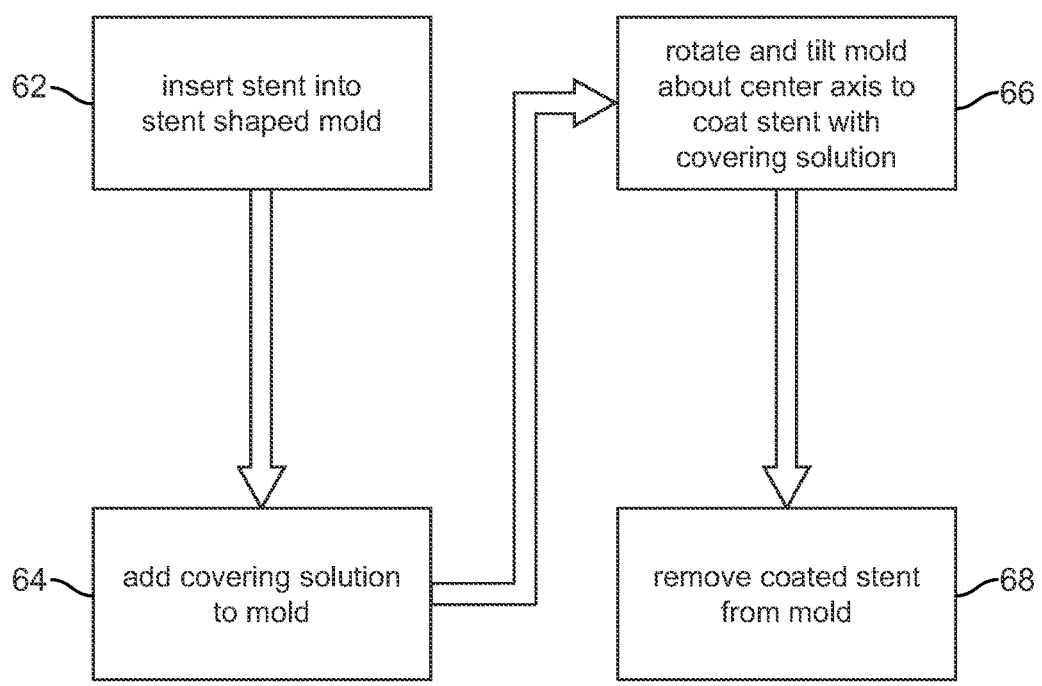
FIG. 10 is a flow chart of a process for covering a stent, according to still another embodiment of the disclosed inventions.

After the stent 10 is formed and the mandrel 30 is removed, the stent 10 can be substantially covered with polymer 14 through various methods (e.g., dipping, spraying, sandwiching, heat shrinking or electro-spinning). In the embodiment shown in FIG. 10, the stent 10 is inserted 62 into an interior of a mold configured to mimic the exterior shape of the stent 10. Then a covering solution is added 64 to the interior of the mold. Next, mold is rotated and tilted 66 about its center axis to cover the stent 10 with the covering solution. Finally, the covered stent 10 is removed 68 from the mold. Heat can be added to the process for solvent evaporation and/or curing. The formed and covered stent 10 can be implanted during an endoscopic procedure. During the procedure, the stent 10 is mounted on a delivery device for delivery under direction vision or under fluoroscopy. In the embodiment shown in FIG. 11, a stent 10 made from a shape memory polymer is delivered over an inflatable balloon or a mechanically expandable basket that is expanded in-situ to impart the desired shape to the stent 10.

Shape memory polymers generally have both hard and soft molecular structures, which are relative terms relating to the transition temperature of the segments. These "segments" are blocks or sequences of polymer forming part of the shape memory polymer. Typically, hard segments have a higher glass transition temperature (Tg) than soft segments. Shape memory polymers include a class of (meth) acrylate compositions having a first (meth)acrylate monomer with a lower glass transition temperature (Tg typically less than 25° C.) and a second (meth)acrylate monomer with a higher glass transition temperature (Tg typically greater than 25° C.).

Shape memory polymers, e.g., thermoplastic and thermoset (covalently cross-linked) polymeric materials, used for forming stents 10 may include elastomers that are typically crosslinked and/or crystalline and exhibit melt or glass transitions at temperatures that are above body temperature and safe for use in the body (e.g., at about 40° C. to about 50° C.). Such shape memory polymers include those that maintain stent geometry under expansion conditions without fracture or substantial irreversible stress relaxation or creep. Typically, the stent 10 may be heated to or above the melt or glass transition temperature of the shape memory polymer during expansion. In these temperatures, the polymer may be in a softened state. After the stent 10 is fully expanded and cooled, the shape memory polymer substantially sets in the desired shape and location (e.g., adjacent a leak site). The polymer can have some elastomeric properties in the cooled, hardened state so that the stent 10 can flex with natural body motion. After cooling, the stent 10 exhibits sufficient resistance to inward radial force to keep a body lumen open. After the leaks have healed, the stent 10 may be softened by heating for removal.

Figure 11:
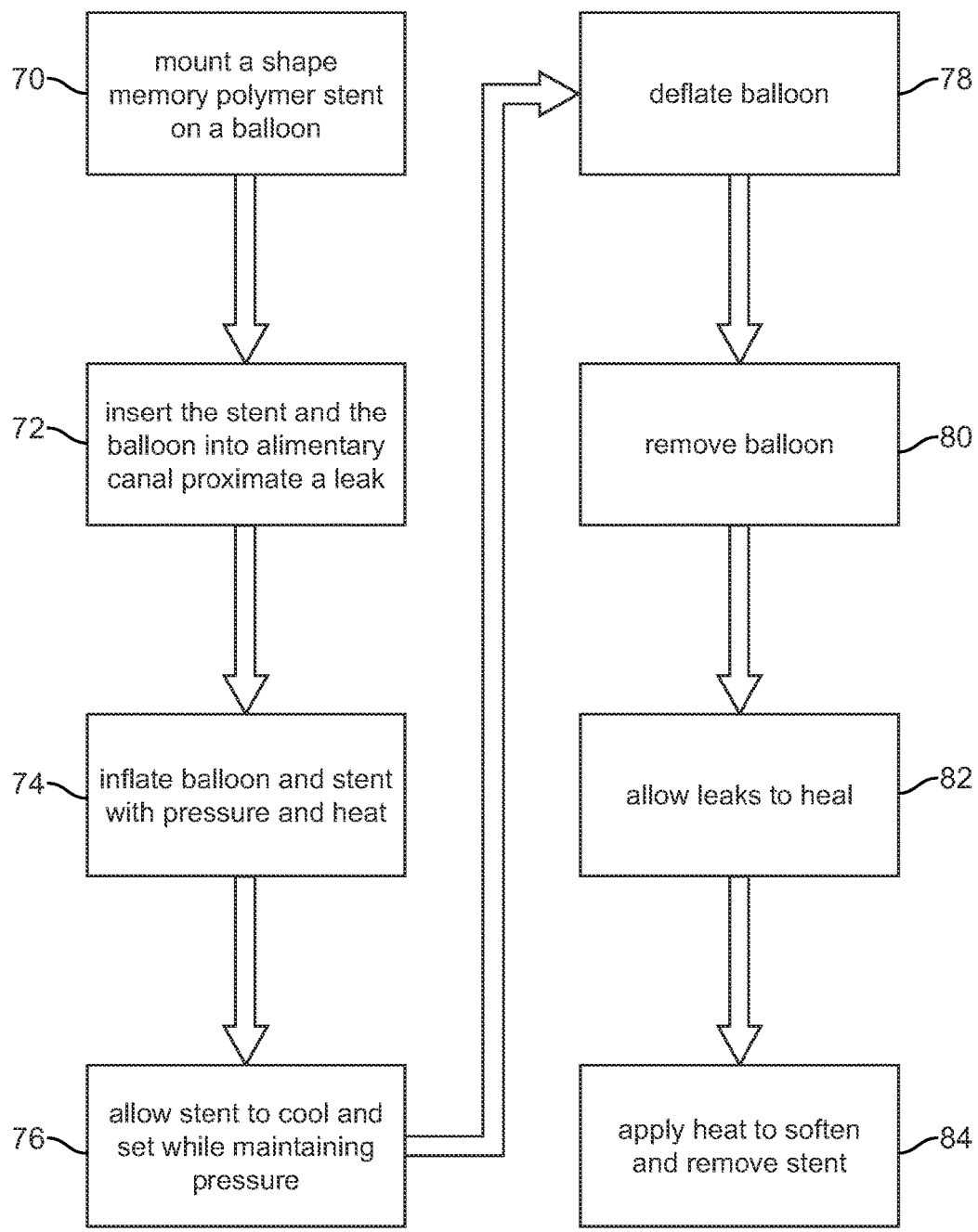
FIG. 11 is a flow chart of a method of repairing post-anastomasis surgery leaks using a shape memory polymer stent according to still another embodiment of the disclosed inventions.

Referring to FIG. 11, a leak is repaired by first mounting 70 a shape memory polymer stent 10 on an expandable device, such as (without limitation) an inflatable balloon or a mechanically expandable basket. The expandable device and stent 10 are then inserted 72 into the alimentary canal proximate a leak. Next, the expandable device is then expanded, thereby expanding the stent 10 against the leak. In the embodiment of FIG. 11, the expandable device is a balloon that is expanded 74 by application of pressure, and heat is added to thereby soften the stent to allow for its in-situ expansion. The application of added heat is stopped, and the stent 10 is allowed to cool and set 76, while the expanded size of the balloon is maintained in order to form the desired shape of the stent 10. Next, the balloon is deflated 78 by removing the application of pressure, and the balloon is removed 80 from the stent through the alimentary canal. After the leaks have healed 82, the stent may (optionally) be removed by softening the stent with the application of heat 84.

While various embodiments of the disclosed inventions have been shown and described, it should be appreciated that they are presented for purposes of illustration, and not limitation. It will be appreciated that various modifications may be made to the illustrated and described embodiments without departing from the scope of the disclosed inventions, which is to be defined only by the following claims and their equivalents.

What is claimed is:

1. A single stent for repairing post-anastomosis surgery leaks, comprising:
    a single elongated tube, the single elongated tube is woven, braided or knit, the single elongated tube having a shape that includes, in order from a proximal end to a distal end of the single elongated tube:
        a proximal flare-shaped flange that includes a proximal cylindrical portion and a distal truncated cone portion,
        a proximal cylindrical segment,
        an enlarged middle section,
        a distal cylindrical segment, and
        a distal flare-shaped flange that includes a proximal truncated cone portion and a distal cylindrical portion,
    wherein the distal cylindrical segment has a diameter that is smaller than a diameter of the proximal cylindrical segment, wherein the enlarged middle section has a diameter that is larger than the proximal flare-shaped flange, the proximal cylindrical segment, the distal cylindrical segment, and the distal flare-shaped flange, the enlarged middle section has a symmetrical shape, the single stent having an interior surface and an exterior surface and wherein an entirety of the exterior surface of the elongated tube from the proximal cylindrical segment to the distal cylindrical segment is covered with a polymer cover configured to seal leaks and prevent tissue in-growth into the single elongated tube.

2. The stent of claim 1, wherein the single elongated tube is self expanding.

3. The stent of claim 1, wherein the single elongated tube is formed from an alloy, a polymer, or a combination thereof.

4. The stent of claim 1, wherein the single elongated tube is radiopaque, the tube comprises a radiopaque marker, or a combination thereof.

5. The stent of claim 1, the single elongated tube further comprising a valve configured to prevent reflux through the stent.

6. The stent of claim 1, further comprising a removal loop.

7. The stent of claim 1, wherein the exterior surface of the single elongated tube is coated with a therapeutic agent.

8. The stent of claim 1, wherein the single elongated tube is formed from a biodegradable polymer.

9. The stent of claim 1, wherein the cover is a biodegradable polymer.

10. The stent of claim 1, wherein the distal cylindrical portion of the distal flare-shaped flange has a diameter that is smaller than a diameter of the proximal cylindrical portion of the proximal flare-shaped flange.

11. A single stent for repairing post-anastomosis surgery leaks, comprising:
  a single elongated tube having a proximal portion and a distal portion separated by an enlarged middle portion, the proximal portion including first and second proximal cylindrical portions separated by a first truncated cone portion, the first proximal cylindrical portion located proximal of the second proximal cylindrical portion, the distal portion including first and second distal cylindrical portions separated by a second truncated cone portion, the first distal cylindrical portion located proximal of the second distal cylindrical portion, wherein the second proximal cylindrical portion has a diameter larger than a diameter of the first distal cylindrical portion, wherein the enlarged middle portion has a diameter that is larger than a diameter of any other portion of the tube, the tube having an interior surface and an exterior surface; and
  a polymer cover disposed over the entire exterior surface of the tube from the proximal portion to the distal portion, the polymer cover configured to seal leaks and prevent tissue in-growth into the tube.

12. The stent of claim 11, wherein the single elongated tube is self-expanding.

13. The stent of claim 11, wherein the single elongated tube is formed from an alloy, a polymer, or a combination thereof.

14. The stent of claim 11, wherein the single elongated tube is radiopaque, the tube comprises a radiopaque marker, or a combination thereof.

15. The stent of claim 11, the single elongated tube further comprising a valve configured to prevent reflux through the stent.

16. The stent of claim 11, further comprising a removal loop.

17. The stent of claim 11, wherein the polymer cover comprises or is coated with a material that swells in situ.

18. The stent of claim 11, wherein the cover is a biodegradable polymer.

19. The stent of claim 11, wherein the first proximal cylindrical portion has a diameter larger than a diameter of the second distal cylindrical portion.

20. A single stent for repairing post-anastomosis surgery leaks, comprising:
  a single elongated tube having:
    a proximal flare-shaped flange that includes a proximal cylindrical portion and a distal truncated cone portion,
    a proximal cylindrical segment,
    an enlarged middle section,
    a distal cylindrical segment, and
    a distal flare-shaped flange that includes a proximal truncated cone portion and a distal cylindrical portion,
    wherein the distal cylindrical segment has a diameter that is smaller than a diameter of the proximal cylindrical segment, wherein the proximal and distal cylindrical segments are directly connected to the enlarged middle section, wherein the enlarged middle section has a diameter that is larger than a diameter of any other region of the single elongated tube;
  a polymer cover disposed over an entirety of an exterior surface of the single elongated tube such that the polymer cover seals leaks and prevents tissue in-growth into the single elongated tube; and
  a valve, disposed within the single elongated tube, the valve configured to prevent reflux through the stent.

* * * * *